US012661812B2

(12) United States Patent
Burr et al.

(10) Patent No.: US 12,661,812 B2
(45) Date of Patent: Jun. 23, 2026

(54) GLOVE ARRANGEMENT FOR A BARRIER SYSTEM

(71) Applicant: Bioquell UK Limited, Andover (GB)

(72) Inventors: Stewart Burr, Andover (GB); Skipp Savage, Andover (GB); Robin Pitt, Andover (GB)

(73) Assignee: Bioquell UK Limited, Andover (GB)

( * ) Notice: Subject to any disclaimer, the term of this patent is extended or adjusted under 35 U.S.C. 154(b) by 1043 days.

(21) Appl. No.: 17/781,937

(22) PCT Filed: Nov. 27, 2020

(86) PCT No.: PCT/GB2020/053030
§ 371 (c)(1),
(2) Date: Jun. 2, 2022

(87) PCT Pub. No.: WO2021/111111
PCT Pub. Date: Jun. 10, 2021

(65) Prior Publication Data
US 2022/0331996 A1 Oct. 20, 2022

(30) Foreign Application Priority Data

Dec. 5, 2019 (GB) ...................................... 1917801

(51) Int. Cl.
*B25J 21/02* (2006.01)
*A61L 2/10* (2026.01)
(Continued)

(52) U.S. Cl.
CPC ................. *B25J 21/02* (2013.01); *A61L 2/10* (2013.01); *A61L 2/208* (2013.01); *B01L 1/025* (2013.01); *B01L 2200/082* (2013.01)

(58) Field of Classification Search
CPC ................................... B25J 21/02; G21F 7/053
See application file for complete search history.

(56) References Cited

U.S. PATENT DOCUMENTS 3,391,406 A 7/1968 Jean
4,123,123 A 10/1978 Sato et al.
(Continued)

FOREIGN PATENT DOCUMENTS

BE 761829 A 7/1971
CN 205704286 U 11/2016
(Continued)

OTHER PUBLICATIONS

Machine Translation of "Hirosawa", JP 2015116622 A, cited in IDS filed Jun. 2, 2022 (Year: 2015).*
(Continued)

*Primary Examiner* — Jennifer Wecker
*Assistant Examiner* — Brady C Pilsbury
(74) *Attorney, Agent, or Firm* — Fredrikson & Byron, P.A.

(57) ABSTRACT

The present disclosure relates to a glove arrangement (20) for mounting to a barrier wall (15) of a barrier system (10) comprising a sleeve arrangement (21). The first and second sleeves (40, 41) comprise first and second internal surfaces (90, 91). The intermediate sleeve (40) comprises an intermediate internal surface (92), an outer perimeter (61) attached to the first sleeve (40) and an inner perimeter (62) attached to the second sleeve (41), the outer perimeter (61) having a greater diameter than the inner perimeter (62). In an extended configuration the first sleeve (40) extends from the second and intermediate sleeves (40) for use during manipulation of the glove (22) by an operator. In a retracted configuration the second sleeve (41) is retracted at least partially inside the first sleeve (40) about the intermediate sleeve (40) such that the first and second internal surfaces (90, 91) at least partially face each other. The intermediate sleeve (40) separates the intermediate internal surface (92) from itself and from the first and second internal surfaces (Continued)

(90, 91) to form a cavity (48) between the first, second and intermediate internal surfaces (90, 91, 92).

19 Claims, 8 Drawing Sheets

(51) Int. Cl.
      *A61L 2/208*          (2026.01)
      *B01L 1/02*           (2006.01)

(56)                    References Cited

U.S. PATENT DOCUMENTS

| | | | |
|---|---|---|---|
| 4,141,609 | A | 2/1979 | Eisert |
| 4,156,146 | A | 5/1979 | Imai et al. |
| 5,299,243 | A | 3/1994 | Picco |
| 5,380,078 | A | 1/1995 | Baczkowski et al. |
| 5,662,581 | A | 9/1997 | Jennrich et al. |
| 5,833,911 | A | 11/1998 | Llort et al. |
| 9,524,805 | B2 | 12/2016 | Mazaudier et al. |
| 9,589,689 | B2 | 3/2017 | Fournier |
| 2016/0166455 | A1* | 6/2016 | Steinert .................. A61B 42/10 600/21 |
| 2018/0303170 | A1 | 10/2018 | Moussa et al. |

FOREIGN PATENT DOCUMENTS

| | | | |
|---|---|---|---|
| EP | 483025 | B1 | 8/1994 |
| EP | 1265257 | B1 | 10/2010 |
| EP | 2188095 | B1 | 2/2011 |
| EP | 3383602 | A4 | 8/2019 |
| FR | 1426453 | A | 1/1966 |
| GB | 1092441 | A | * 11/1967 ......... A41D 19/0062 |
| GB | 1436104 | A | 5/1976 |
| JP | S56140232 | A | 11/1981 |
| JP | H08285986 | A | 11/1996 |
| JP | 2625607 | B2 | 7/1997 |
| JP | 2995627 | B1 | 12/1999 |
| JP | 2001328093 | A | 11/2001 |
| JP | 2004294159 | A | 10/2004 |
| JP | 2006198280 | A | 8/2006 |
| JP | 3981668 | B2 | 9/2007 |
| JP | 4029075 | B2 | 1/2008 |
| JP | 4317991 | B2 | 8/2009 |
| JP | 3163435 | U | 10/2010 |
| JP | 2013203452 | A | 10/2013 |
| JP | 2015116622 | A | 6/2015 |
| WO | 1998024599 | A1 | 6/1998 |
| WO | 2014072229 | A1 | 5/2014 |
| WO | 2019079099 | A1 | 4/2019 |

OTHER PUBLICATIONS

Machine Translation of "Huang", CN 205704286 U, cited in IDS filed Jun. 2, 2022 (Year: 2016).*
GB Patent Application No. GB1917801.1, Combined Search and Examination Report dated May 28, 2020, 5 pages.
GB Patent Application No. GB1917801.1, further Combined Search and Examination Report dated Nov. 27, 2020, 4 pages.
GB Patent Application No. GB2116162.5, Combined Search and Examination Report dated Apr. 29, 2022, 4 pages.
Bioquell "The Bioquell Qube a Modular Isolator with Integrated Decontamination", Mar. 11, 2019, pp. 1-3.
International Search Report for International Application No. PCT/GB2020/053030, dated Mar. 2, 2021, 3 pgs.

* cited by examiner

GLOVE ARRANGEMENT FOR A BARRIER SYSTEM

TECHNICAL FIELD

The present disclosure is directed towards a glove arrangement for mounting to a barrier wall of a barrier system, a barrier system comprising such a glove arrangement, a method of manufacturing such a glove arrangement and a method of operating such a barrier system. The present disclosure is further directed towards an insert, a glove arrangement comprising such an insert, a barrier system comprising such an insert and a method of operating such a barrier system.

BACKGROUND

Barrier systems usually comprise a barrier wall, which is typically transparent, to separate a work process area from an operator area. An exemplary barrier system is an isolator, such as that disclosed in WO-A-2013/186518, in which the work process area is isolated and sealed from the operator area in order to prevent contamination of the work process area by the environment of the operator area and vice-versa. In an isolator the work process area may be operated at a negative or positive pressure to assist in isolating it from the operator area. The work process area may be periodically decontaminated, for example by directing sterilant gas or vapour therethrough. A particularly suitable decontaminant is hydrogen peroxide vapour, as discussed in WO-A-2013/186518.

In barrier systems glove arrangements typically extend through apertures in the barrier wall. Each glove arrangement typically comprises a glove mounted to a sleeve, for receiving the operator's hand and arm respectively, and the sleeve is mounted to the barrier wall. The glove arrangement is typically flexible to enable easy manipulation and movement within the work process area. The glove may be removably mounted to the sleeve such that it is replaceable separately to the sleeve or the glove and sleeve may be integrally formed as a gauntlet. An operator can locate their hands and arms in the gloves and sleeves such that, whilst remaining within the operator area, they can use the gloves to perform work in the work process area. Examples of such work include preparing pharmaceutical prescriptions or the like.

In a decontamination cycle it is necessary to thoroughly decontaminate the surfaces of the glove arrangement in addition to the surfaces of the work process area. During decontamination the glove and sleeve may be fully extended into the work process area. Such a configuration is discussed in U.S. Pat. No. 5,662,581, which also discloses minimising the sealing contact between the sleeve and the barrier wall, or between the glove and sleeve, in order to improve decontamination. However, in this configuration the glove and sleeve can interfere with items in the work process area. In an alternative configuration, the glove and sleeve can be fully extended out of the work process area into the operator area during decontamination. However, the decontaminant may not reach the fingers of the glove due to their distance from decontaminant flow in the work process area. In either of the aforementioned fully extended configurations folds are preferably avoided to prevent contact or occlusions between surfaces of the sleeve and glove where decontaminant may not reach. For example, a rigid frame may be located inside or outside the glove arrangement to hold it in a stretched configuration without folds.

A further alternative is to double or fold the sleeve back upon itself to alleviate some of the shortcomings of the aforementioned configurations. The glove fingers are in or near the work process area such that they are effectively decontaminated. As the glove and sleeve do not extend far into the work process area they do not interfere with items therein. However, in such a configuration surfaces of the sleeve and glove are in contact at folds, pinch points or other such occlusions and the decontaminant may not reach such surfaces. In addition, during testing biological indicators may be used to indicate whether decontaminant has reached certain areas. The decontaminant may not reach any biological indicators placed at the folds or pinch points and they may therefore not demonstrate that decontamination has occurred.

SUMMARY

An object of the present disclosure is to provide an improved glove arrangement, barrier system, method of manufacture, method of operation and insert. A further object is to provide a sleeve arrangement, glove arrangement and barrier system that can be more effectively decontaminated.

The present disclosure therefore provides a glove arrangement for mounting to a barrier wall of a barrier system and comprising a sleeve arrangement, the sleeve arrangement comprising: a first sleeve for mounting around an aperture through the barrier wall and comprising a first internal surface; a second sleeve for mounting a glove thereto and comprising a second internal surface; and an intermediate sleeve comprising an intermediate internal surface, an outer perimeter attached to the first sleeve and an inner perimeter attached to the second sleeve, the outer perimeter having a greater diameter than the inner perimeter, wherein the sleeve arrangement is configurable between: an extended configuration in which the first sleeve extends from the second and intermediate sleeves for use during manipulation of the glove by an operator; and a retracted configuration in which: the second sleeve is retracted at least partially inside the first sleeve about the intermediate sleeve such that the first and second internal surfaces at least partially face each other; and the intermediate sleeve separates the intermediate internal surface from itself and from the first and second internal surfaces to form a cavity between the first, second and intermediate internal surfaces.

The present disclosure further provides a method of manufacturing the aforementioned glove arrangement, wherein the method comprises moulding the sleeve arrangement in the retracted configuration.

The present disclosure further provides a barrier system comprising: a barrier wall at least partially separating an operator area from a work process area and comprising at least one aperture therethrough; and at least one aforementioned glove arrangement, the first sleeve being mounted to the barrier wall around the at least one aperture, wherein in the extended configuration the second sleeve, intermediate sleeve and at least part of the first sleeve are located in the work process area and in the retracted configuration the intermediate sleeve and at least part of the first and second sleeves are located in the operator area.

The present disclosure further provides a method of operating the aforementioned barrier system comprising: configuring the sleeve arrangement in the extended configuration and manipulating the glove arrangement to perform work in the work process area; and configuring the sleeve arrangement in the retracted configuration directing a decontaminant into the work process area to decontaminate the first, second and intermediate internal surfaces.

The retracted configuration is suitable for use during decontamination of the sleeve arrangement. The cavity is suitable for decontaminant to pass through and contact the first, second and intermediate internal surfaces. Due to the separation therebetween, no occlusions can form at pinch points and folds as in the prior art systems. As a result, effective and complete decontamination of the internal surface of the sleeve arrangement can be achieved. The decontaminant may therefore also reach any biological indicators located on or around the intermediate sleeve and therefore the biological indicators may show decontamination.

The sleeve arrangement may be adjusted from the retracted configuration to the extended configuration by moving the first sleeve substantially along an extension direction and may be adjusted from the extended configuration to the retracted configuration along a retraction direction. The extension direction may be substantially opposite to the retraction direction. In the extended configuration the first sleeve may extend to the intermediate sleeve along the extension direction and the second sleeve may extend from the intermediate sleeve along the extension direction. In the retracted configuration the first sleeve may extend to the intermediate sleeve along the retraction direction, the second sleeve may extend from the intermediate sleeve along the extension direction and the intermediate sleeve may form the change of direction of extension of the sleeve arrangement between the extension and retraction directions.

The present disclosure further provides a glove arrangement for mounting to a barrier wall of a barrier system comprising: a glove mounted to a sleeve arrangement and/or mounted to a cuff mounted to the sleeve arrangement; and an insert mounted to the cuff and/or sleeve arrangement and at least partially extending from the cuff and/or sleeve arrangement into the glove for supporting the glove.

The insert may comprise an insert coupling for selectively mounting to an insert mount of the cuff and/or sleeve arrangement. The insert may extend between an insert inner end and an insert outer end and comprises an insert wrist portion, for contacting a wrist of the glove, extending from the insert inner end and an insert hand portion, for contacting a hand of the glove, extending from the insert wrist portion to the insert outer end. The insert hand portion may be wider than the insert wrist portion. The insert may curve downwardly from the cuff and/or sleeve arrangement. The thickness of the insert may decrease from the cuff and/or sleeve arrangement.

The present disclosure further provides a barrier system comprising the aforementioned glove arrangement mounted to a barrier wall.

The present disclosure further provides method of operating the aforementioned barrier system comprising mounting the insert to the cuff and/or sleeve arrangement and directing a decontaminant into the work process area to decontaminate the glove, sleeve arrangement and, if present, cuff, wherein during decontamination the inserts supports the glove such that it does not fold back upon and contact itself and/or does not contact the barrier wall, sleeve arrangement and/or cuff.

The present disclosure further provides and insert for supporting a glove of a glove arrangement mounted to a barrier wall and comprising a cuff and/or sleeve arrangement to which the glove is mounted, wherein the insert comprises: an insert wrist portion for mounting to the cuff and/or sleeve arrangement; and an insert hand portion extending from the insert wrist portion for extending from the sleeve arrangement into the glove for supporting the glove during decontamination.

The barrier system of the present disclosure may be any barrier system comprising a barrier wall separating a work process area from an operator area and comprising a glove arrangement for allowing manipulation of objects in the work process area by an operator in the operator area. The work process area may be within an enclosure sealed and isolated from the operator area and preferably the barrier system comprises an isolator. Alternatively, the barrier system may comprise a restricted access barrier system, glove box, aseptic enclosure, a filling line, a process line separated but not sealed from an operator area by a barrier wall or the like.

BRIEF DESCRIPTION OF THE DRAWINGS

By way of example only, embodiments of a glove arrangement, barrier system, method of manufacture, method of operation and insert in accordance with the present disclosure are now described with reference to, and as shown in, the accompanying drawings, in which.

DETAILED DESCRIPTION

Figure 1:
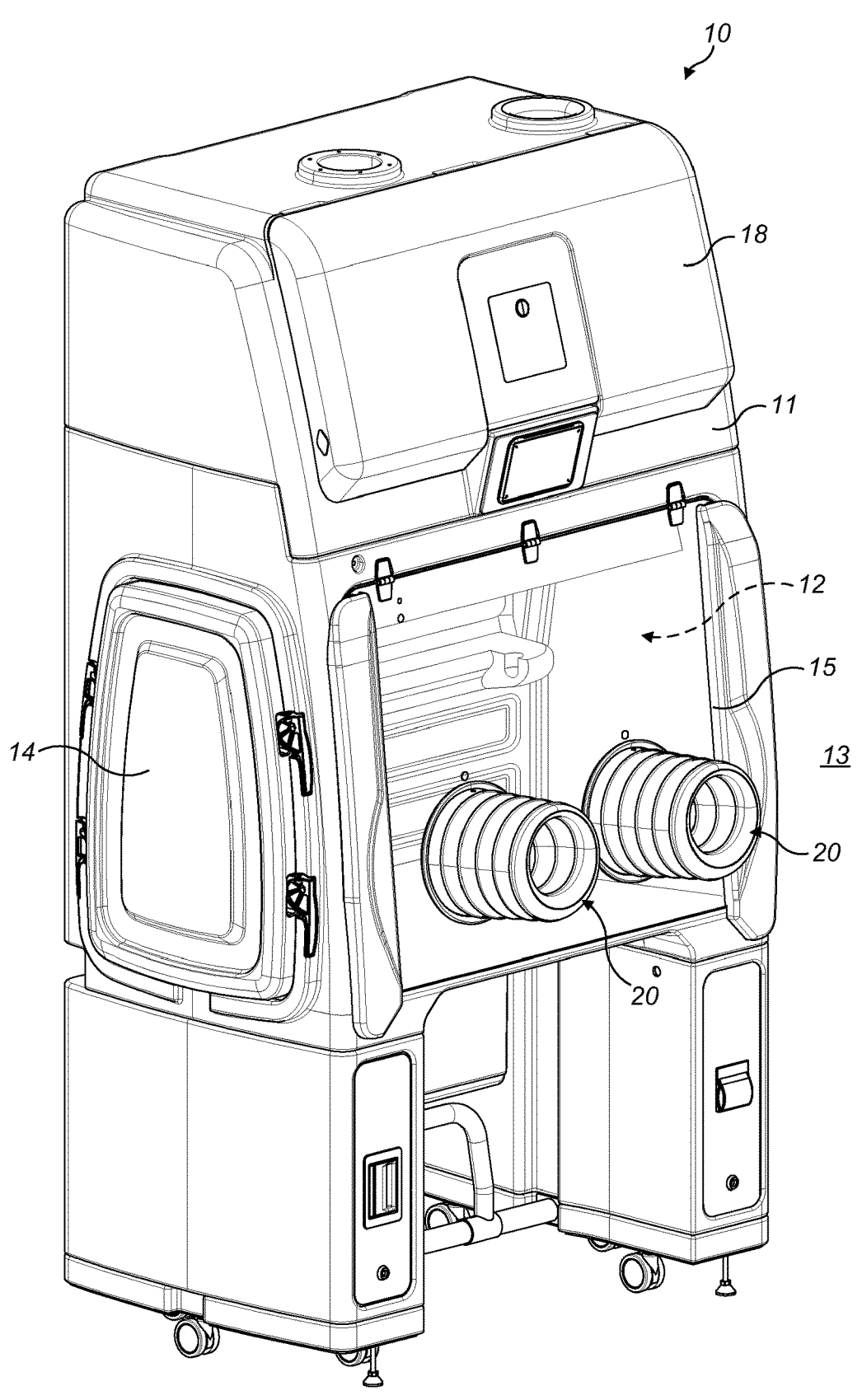
FIG. 1 is a perspective view of an embodiment of a barrier system in accordance with the present disclosure.

FIG. 1 illustrates a barrier system 10, in this example an isolator, in accordance with the present disclosure. The barrier system 10 may comprise an enclosure 11 having a work process area 12 therein. The enclosure 11 may allow the work process area 12 to be sealed from the external environment or operator area 13 and may comprise at least one sealable access port 14. The at least one port 14 may allow the isolator to be connected to another isolator.

The work process area 12 is at least partially separated from the operator area 13 by a barrier wall 15, which may be transparent for an operator to view the work process area 12. The barrier wall 15 may also be openable to allow access to the work process area 12. The barrier wall 15 comprises at least one, preferably two, wall aperture(s) 16 therethrough. A wall mount 17 may extend around the edge of the or each wall aperture 16 and may comprise a, preferably annular (e.g. elliptical, including circular or oval, or the like) flange as illustrated. The wall mount 17 may be located on the operator area 13 side of the barrier wall 15 as illustrated, although it may alternatively be located on the work process area 12 side or around the inner edge of the wall aperture 16.

The barrier system 10 may comprise a decontamination system 18, which may for example comprise an airflow circuit with a fan, for directing a decontaminant through the work process area 12 to decontaminate the surfaces therein. The decontamination system 18 may be mounted to the enclosure 11 as illustrated. Alternatively, the decontamination system 18 may comprise a separate decontamination device located in the work process area 12 or outside of the work process area 12 and in fluid communication therewith via at least one hose or the like. The decontaminant may be a gas or vapour and a particularly suitable decontaminant is hydrogen peroxide vapour. Alternatively or in addition the decontamination system 18 may direct ultraviolet light towards the surfaces.

The barrier system 10 comprises at least one glove arrangement 20 mounted to and extending from the barrier wall 15 into the work process area 12 and/or operator area 13. The barrier system 10 may comprise at least one pair of glove arrangements 20 as illustrated, each glove arrangement 20 of each pair differing only in that they are arranged for the left and right hands of the operator. Each glove arrangement 20 may be mounted around a wall aperture 16 and to a wall mount 17. The at least one glove arrangement 20 may be usable by an operator to manipulate items in the work process area 12 and perform work therein, such as preparing pharmaceutical prescriptions in an isolator, manage items on a process line or the like. The glove arrangements 20 may enable the operator to remain in the operator area 13 whilst performing such work in the work process area 12. The operator may be a human or a machine.

Figure 2:
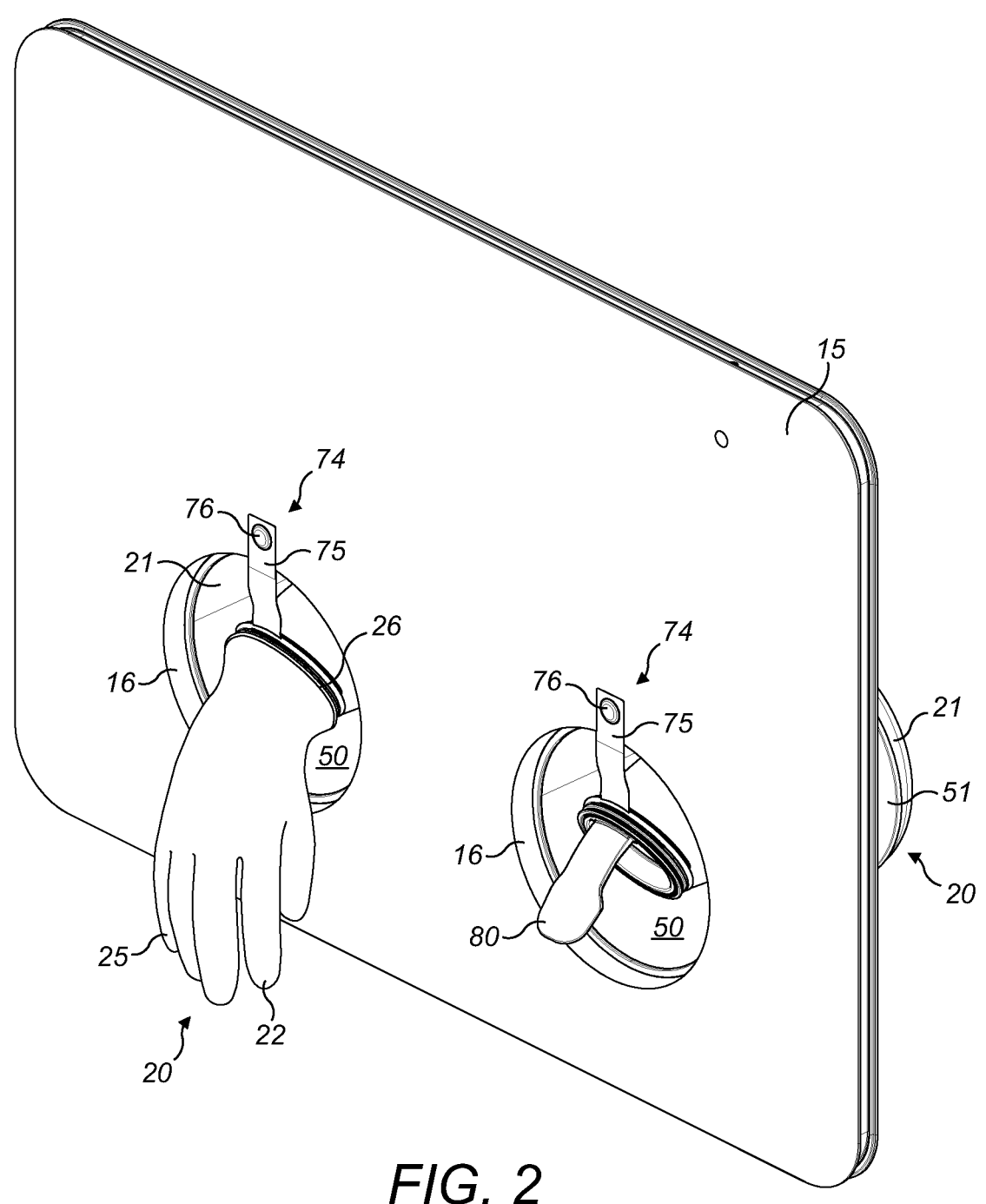
FIG. 2 is a perspective view from a work process area side of a barrier wall and glove arrangements of the barrier system of FIG. 1.
Figure 3:
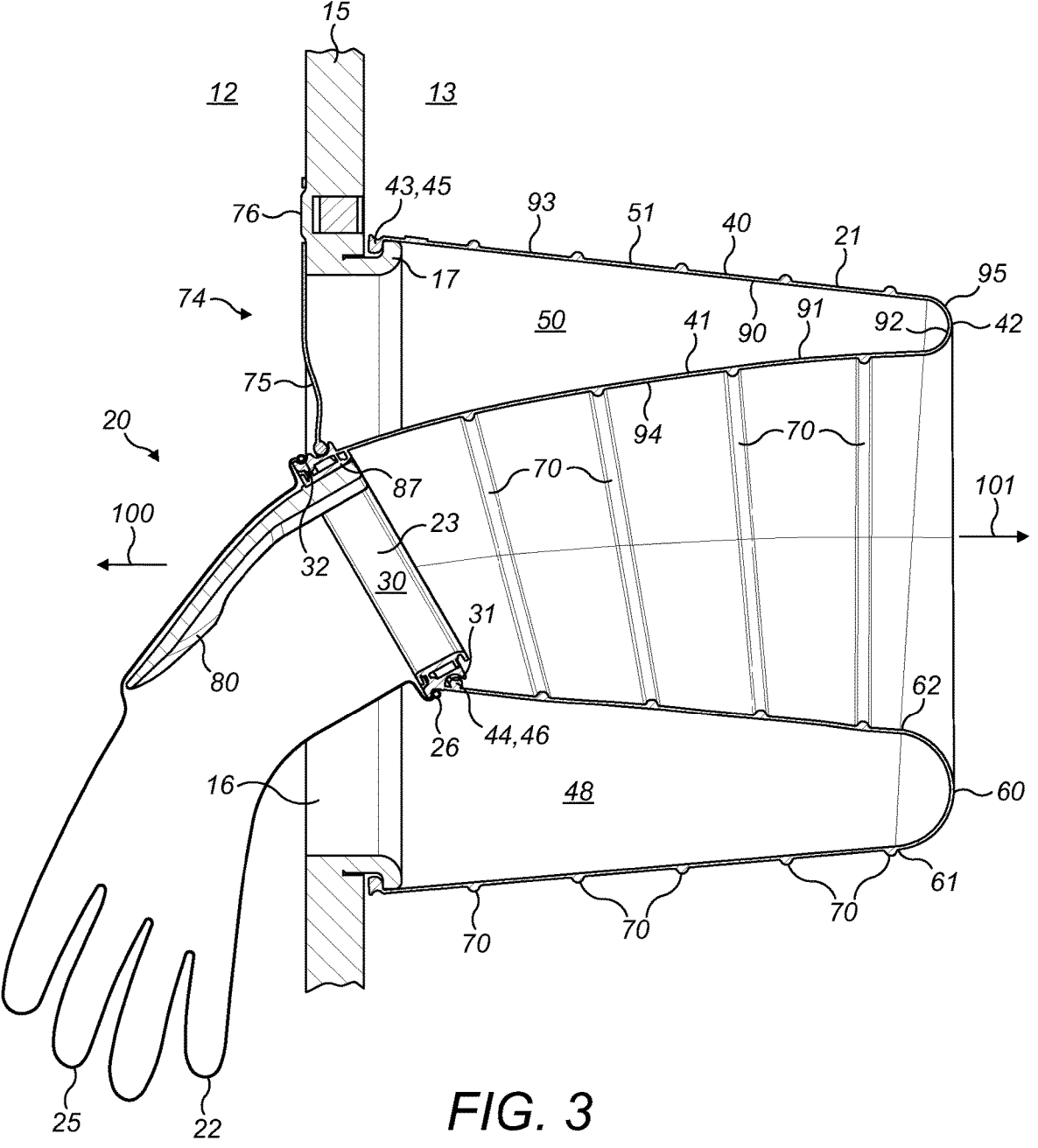
FIG. 3 is a cross-sectional side view of the barrier wall and a glove arrangement of the barrier system of FIG. 1 with the glove arrangement in a retracted configuration.
Figure 4:
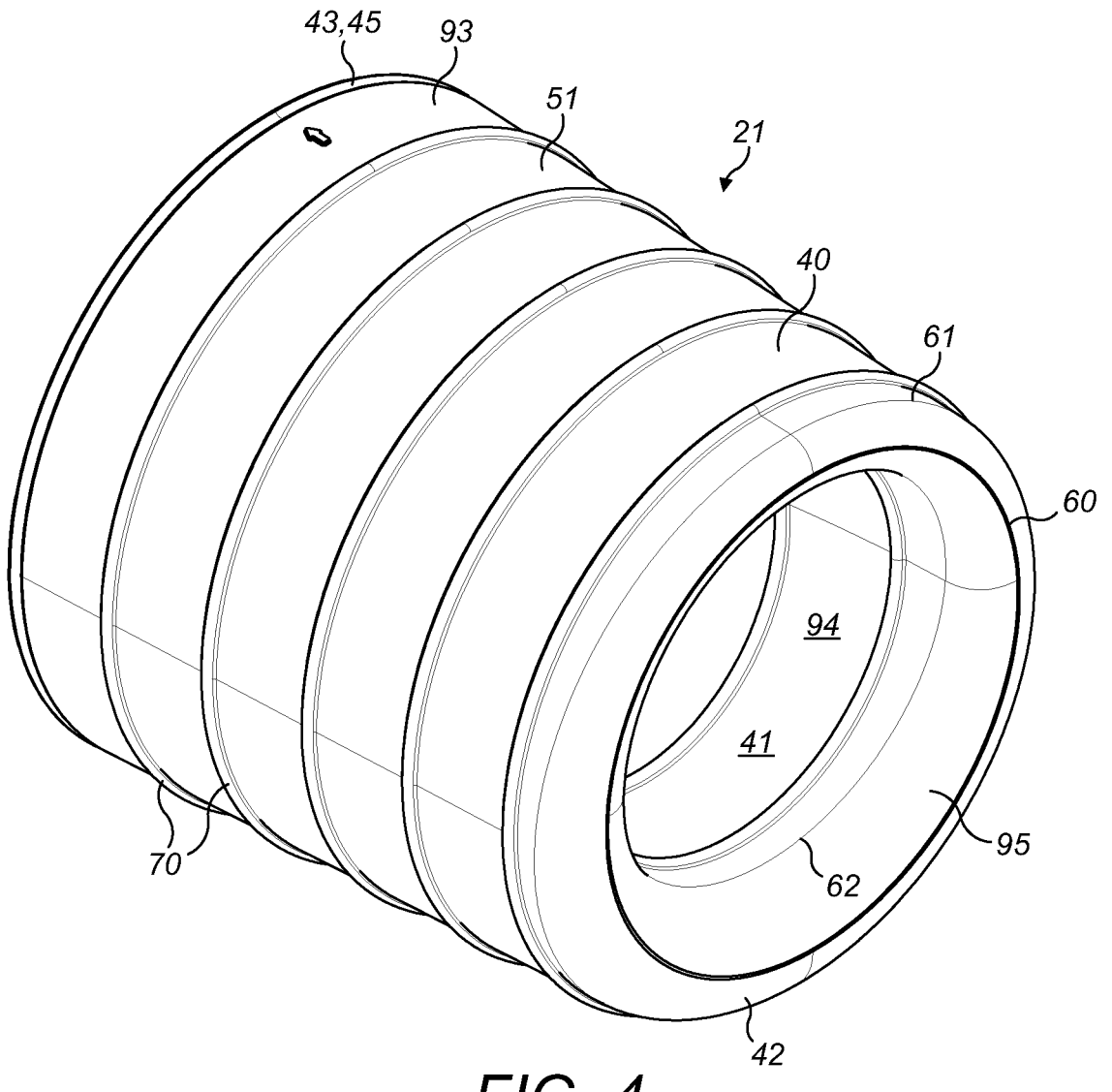
FIG. 4 is a perspective view from an operator area side of a sleeve arrangement of the glove arrangement of the barrier system of FIG. 1.
Figure 5:
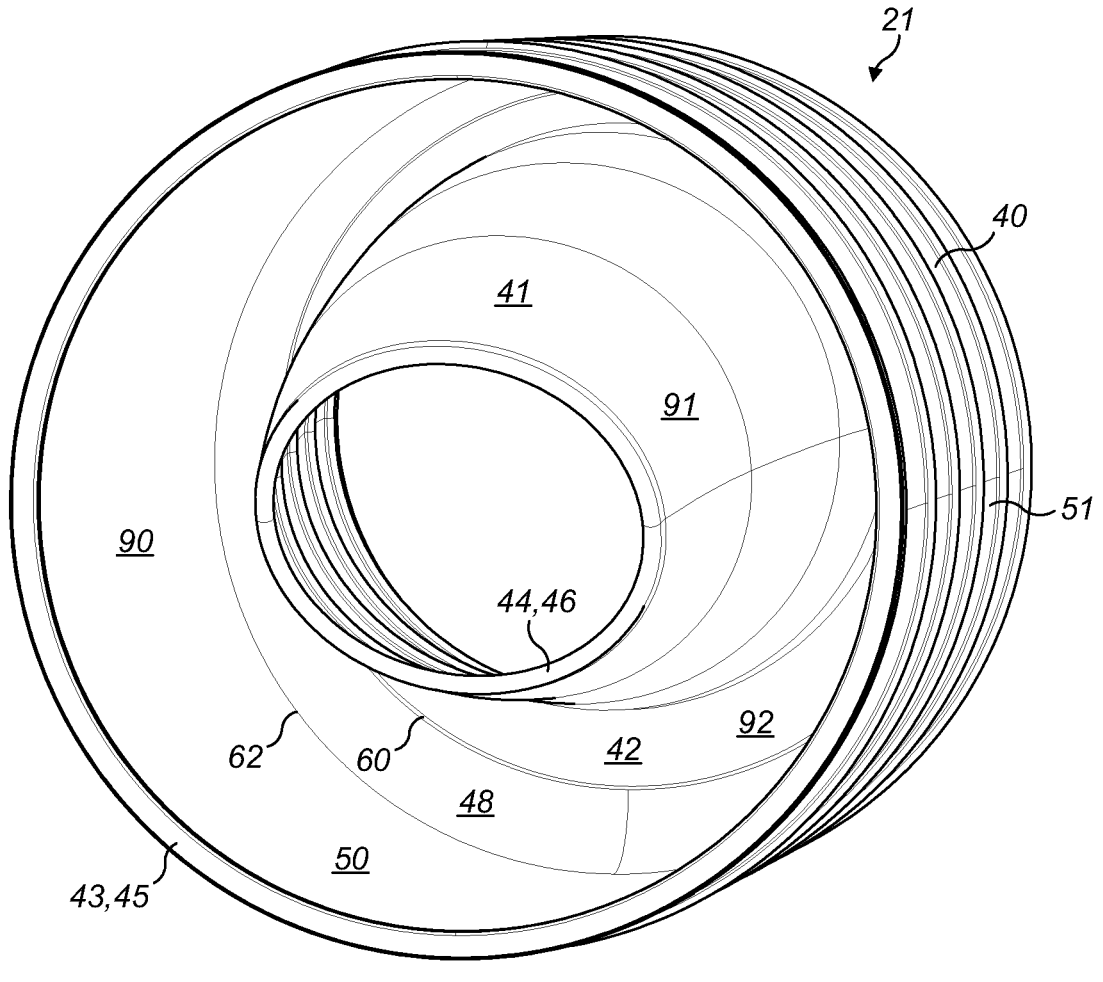
FIG. 5 is a perspective view from a work process area side of the sleeve arrangement of FIG. 4.
Figure 6:
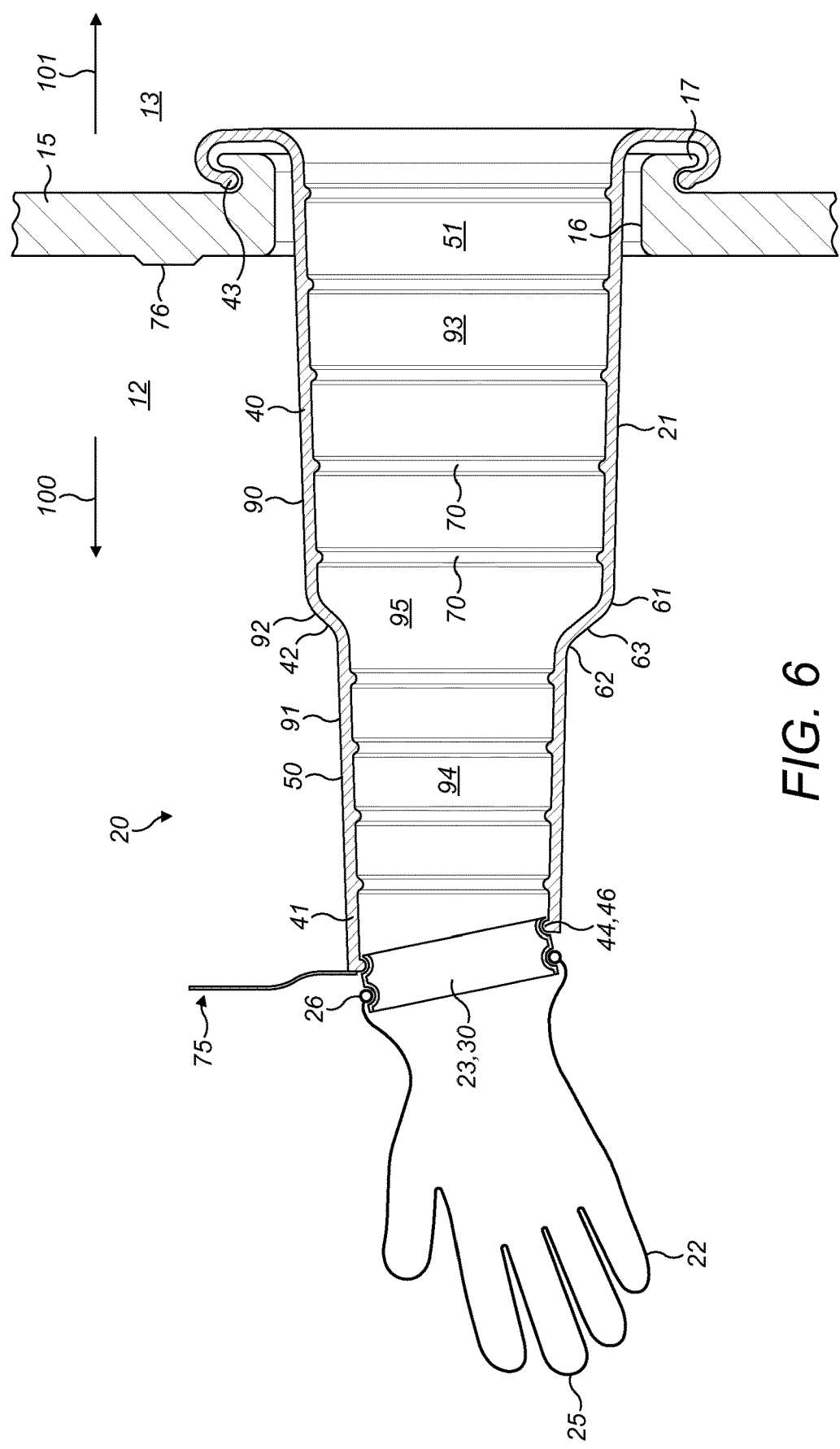
FIG. 6 is a cross-sectional side view of the barrier wall and a glove arrangement of the barrier system of FIG. 1 with the glove arrangement in an extended configuration.

As illustrated further in FIGS. 2, 3 and 6, each glove arrangement 20 comprises a sleeve arrangement 21 and a glove 22 mounted to the sleeve arrangement 21. The glove 22 and sleeve arrangement 21 may be attached to one another by a cuff 23 of the glove arrangement 20 therebetween. The glove 22 may extend between finger tips 25 and a wrist end 26, which may be replaceably mounted to the cuff 23. The glove 22 may comprise a flexible and elastic material for enabling effective manipulation by the operator and may comprise natural rubber latex, neoprene, nitrile, polyurethane, polyvinyl chloride, ethylene propylene diene rubber, chlorosulfonated polyethylene and/or the like.

The cuff 23 may comprise a cuff body 30, which may be in the form of a hollow cylinder or hoop as illustrated. The cuff 23 may comprise a first cuff coupling 31 for the sleeve arrangement 21 to be mounted to and a second cuff coupling 32 for the glove 22 to be mounted to (e.g. by the wrist end 26). In an alternative arrangement the cuff may comprise a ring that clamps the glove 22 to the sleeve arrangement 21 (also known as a one piece cuff ring) or the like.

In an alternative embodiment the glove arrangement 20 may comprise a gauntlet, which may not comprise a cuff 23. In the gauntlet the glove 22 may be mounted and/or formed integrally with the sleeve arrangement 21.

The sleeve arrangement 21 comprises a first sleeve 40, a second sleeve 41 and an intermediate sleeve 42 attached therebetween. As illustrated in FIGS. 3 to 6, the sleeve arrangement 21 may be substantially tubular and comprise an internal surface 50 exposed to the environment of the work process area 12 and an external surface 51 exposed to the environment of the operator area 13. The internal and external surfaces 50, 51 may be formed by the first, second and intermediate sleeves 40, 41, 42. The first, second and intermediate sleeves 40, 41, 42 comprise first, second and intermediate internal surfaces 90, 91, 92 forming the internal surface 50 and may comprise first, second and intermediate external surfaces 93, 94, 95 forming the external surface 51.

The sleeve arrangement 21 may extend between a sleeve wall end 43, which may be formed by the first sleeve 40, and a sleeve glove end 44, which may be formed by the second sleeve 41. The sleeve wall and glove ends 43, 44 may be open and thus form apertures for an operator's arm and hand to pass through.

The first sleeve 40 is mounted around a wall aperture 16 and to the wall mount 17. The first sleeve 40 may comprise a sleeve wall coupling 45 at the sleeve wall end 43 for mounting to the wall mount 17. The sleeve wall coupling 45 may comprise a flange or rib, which may be elastic and flexible, for mounting around the flange of the wall mount 17 and a seal may be formed therebetween.

The second sleeve 41 is configured for the glove 22 to be mounted thereto, such as by the cuff 23 as illustrated. The second sleeve 41 may comprise a sleeve glove coupling 46 at the sleeve glove end 44 for mounting to the glove 22 or cuff 23, for example to the first cuff coupling 31. As illustrated, the sleeve glove coupling 46 may comprise a flange or rib, which is preferably elastic and flexible, for mounting around the recess of the first cuff coupling 31 and forming a seal therebetween. An O-ring or the like may be located around or integrated with the sleeve glove coupling 46 for maintaining the seal. As best shown in FIG. 3, in use the top of the second sleeve 41 may extend further into the work process area 12 than the bottom of the second sleeve 41 and, as a result, the cuff 23 and glove 22 may be directed at an acute angle downwards to limit intrusion of the second sleeve 41 into the work process area 12.

The first and second sleeves 40, 41 may each be tubular and may comprise substantially thin-walled hollow cylinders. The diameter of the second sleeve 41 is less than the diameter of the first sleeve 40 such that the second sleeve 41 fits inside the first sleeve 40 as in FIG. 3. In particular, the minimum diameter of the first internal surface 90 is greater than the maximum diameter of the second internal surface 91. The first and/or second sleeves 40, 41 may be tapered as illustrated. The first sleeve 40 may taper, and thus reduce in diameter, from the sleeve wall end 43 to the intermediate sleeve 42. The second sleeve 41 may taper, and thus reduce in diameter, from the intermediate sleeve 42 to the sleeve glove end 44. In alternative embodiments the first and/or second sleeves 40, 41 may have substantially constant diameters along their lengths such that they are not tapered.

The intermediate sleeve 42 comprises an outer perimeter 61 attached to the first sleeve 40 and an inner perimeter 62 attached to the second sleeve 41. The outer perimeter 61 has a greater diameter than the inner perimeter 62. Thus the intermediate sleeve 42 reduces in diameter along its length. A rate of reduction of diameter along the length of the sleeve arrangement 21 may be greater along the intermediate sleeve 42 than along the length of the first and/or second sleeve 40, 41. The rate of reduction of diameter along the length may be defined as the change in the magnitude of the diameter per unit length of the sleeve arrangement 21. The length may be the dimension along the sleeve arrangement 21 between the sleeve wall and glove ends 43, 44 and may be the dimension parallel to and/or along the centrelines of the first, second and intermediate sleeves 40, 41, 42, particularly in the extended configuration. The diameter may the outer diameter (i.e. the dimension perpendicular to the centrelines of the first, second and intermediate sleeves 40, 41, 42) of the sleeve arrangement 21 when in the extended configuration. If the first and/or second sleeve are not tapered then their rate of reduction of diameter along their length is zero.

The length of the first and/or second sleeve 40, 41 may be at least twice or at least five times the length of the intermediate sleeve 42.

The first, second and intermediate sleeves 40, 41, 42 may be substantially elliptical in cross-section (i.e. a cross-section taken in a plane parallel to the plane of the barrier wall 15) and/or the outer and inner perimeters 61, 62 may be substantially elliptical. They may be circular and/or oval as illustrated and the cross-sectional shape may vary along their length. In other embodiments they may have other shaped cross-sections, such as polygonal or the like.

The sleeve arrangement 21 is configurable between a retracted configuration as illustrated in FIG. 3 and an extended configuration as illustrated in FIG. 6. The extended configuration is for use by the operator to manipulate the glove 22 in the work process area 12 through the barrier wall 15, with their hand inside the glove 22 and their arm inside the sleeve arrangement 21. The retracted configuration may be for storage of the sleeve arrangement 21 and may be for decontamination of the sleeve arrangement 21.

When adjusted from the retracted configuration to the extended configuration the first sleeve 40 and, if present, glove 22 may be moved substantially along an extension direction 100. When adjusted from the extended configuration to the retracted configuration the first sleeve 40 and, if present, glove 22 may be moved substantially along a retraction direction 101. The extension direction 100 may be substantially opposite to the retraction direction 101. The extension and retraction directions 100, 101 may be substantially perpendicular to the plane of the barrier wall 15.

As shown in FIGS. 3 and 6, the first sleeve 40 may turn at least partially inside out when moved from the extended configuration to the retracted configuration. In the illustrated embodiment, in which the wall mount 17 is on the operator area 13 side of the barrier wall 15, the sleeve wall end 43 may also be on the operator area 13 side in both the extended and retracted configurations. The second sleeve 41 may have substantially the same shape in the extended and retracted configurations. The intermediate sleeve 42 may have different shapes in the extended and retracted configurations. The intermediate sleeve 42 may comprise a tubular body 63 in the extended configuration and an annular body 60 in the retracted configuration.

In the extended configuration the second sleeve 41 extends from the first sleeve 40. The first sleeve 40 may extend from the sleeve wall end 43 to the intermediate sleeve 42 along the extension direction 100. The intermediate sleeve 42 may extend from the outer perimeter 61 to the inner perimeter 62 along the extension direction and may thus form the tubular body 63. The second sleeve 41 may extend from the intermediate sleeve 42 to the sleeve glove end 44 along the extension direction 100. At least 50% of the length, preferably all of the length, of the second sleeve 41 may be outside of the first sleeve 40. The second sleeve 41, intermediate sleeve 42 and at least part of the first sleeve 40 are located in the work process area 12. The first, second and intermediate external surfaces 93, 94, 95 may face inwardly towards themselves and the first, second and intermediate internal surfaces 90, 91, 92 may face outwardly away from themselves. The tubular body 63 tapers from the outer perimeter 61 to the inner perimeter 62.

In the retracted configuration the second sleeve 41 is retracted at least partially inside the first sleeve 40 about the intermediate sleeve 42 such that the first and second internal surfaces 90, 91 at least partially face each other. The first external surface 93 may face outwardly from itself and the second external surface 94 may face inwardly towards itself. The intermediate sleeve 42 and at least part of the first and second sleeves 40, 41 may be located in the operator area 13. The first sleeve 40 may extend from the sleeve wall end 43 to the intermediate sleeve 42 along the retraction direction 101. The second sleeve 41 may extend from the intermediate sleeve 42 to the sleeve glove end 44 along the extension direction 100. The intermediate sleeve 42 may form the change of direction of extension of the sleeve arrangement 21 between the extension and retraction directions 100, 101.

The intermediate sleeve 42 separates the intermediate internal surface 92 from itself (i.e. such that any part of the intermediate internal surface 92 is not in contact with or abutting another part of the intermediate internal surface 92) and from the first and second internal surfaces 90, 91 to form a cavity 48 between the first, second and intermediate internal surfaces 90, 91, 92. The intermediate sleeve 42 at least separates the first and second internal surfaces 90, 91 adjacent to the intermediate internal surface 92 and the cavity 48 may extend from the intermediate sleeve 42, between the first and second sleeves 40, 41 and to at least the sleeve wall and/or glove ends 43, 44. The intermediate internal surface 92 may face the cavity 48 between the first and second internal surfaces 90, 91. The cavity 48 is suitable for decontaminant to flow or pass through and contact the first, second and intermediate internal surfaces 90, 91, 92. As a result, occlusions may be avoided and during decontamination decontaminant can effectively move around the cavity 48 to contact substantially all of the first, second and intermediate internal surfaces 90, 91, 92. The internal surface 50 may therefore be effectively decontaminated.

The minimum separation distance between the first and second internal surfaces 90, 91 may be defined by the vertical separation of the outer and inner perimeters 61, 62, which may be defined by the length of the intermediate sleeve 42 and the rate of reduction of diameter along the length of the intermediate sleeve 42. The minimum separation distance between the first and second internal surfaces 90, 91 in the retracted configuration may be at least 3 mm, at least 5 mm or at least 10 mm. The separation distance is preferably sufficiently large for a biological indicator to be located on the intermediate internal surface 92.

The intermediate sleeve 42 is arranged to maintain this separation in the retracted configuration by maintaining its shape in the retracted configuration. This can be achieved by appropriate selection of the material, dimensions and shape of the intermediate sleeve 42. The intermediate sleeve 42 may be resiliently biased to maintain the separation, such as by being formed from an elastic, but reasonably rigid, material. The intermediate sleeve 42 may be substantially resilient to compression of the outer perimeter 61 towards the inner perimeter 62, for example under the weight of the sleeve arrangement 21. The intermediate sleeve 42 may, however, be sufficiently flexible such that it can change between the tubular body 63 and the annular body 60.

As illustrated the intermediate sleeve 42 may therefore comprise the annular body 60 in the retracted configuration. The annular body 60 may be curved from the outer perimeter 61 to the inner perimeter 62 such that it forms a hollow semi-toroid and may curve outwardly and away from the first and second sleeves 40, 41. In the retracted configuration the outer and inner perimeters 61, 62 of the annular body 60 may be substantially aligned with one another in a plane substantially parallel to the barrier wall 15 and/or perpendicular to the extension and retraction directions 100, 101.

The intermediate sleeve 42 may alternatively be substantially rigid to maintain the separation between the outer and inner perimeters 61, 62. For example, although not illustrated, the intermediate sleeve 42 may have the same shape in both the extended and retracted configurations and may comprise a substantially rigid ring, for example in the form of a round annular disc. Such a rigid ring may be formed separately or integrally with the first and second sleeves 40, 41 and may have a very high rate of reduction of diameter (i.e. approaching infinity due to a step change in diameter).

The centre of the inner perimeter 62 may be vertically offset from and may be higher than the centre of the outer perimeter 61. The terms vertically offset means a separation or an offset along the direction of the gravitational force. The outer and inner perimeter 61, 62 may be vertically offset in the same vertical plane in the retracted configuration as in FIG. 3 and may be vertically offset in different parallel vertical planes in the extended configuration as in FIG. 6. In the retracted configuration the cavity 48 may therefore have a greater volume in its lower half than in its upper half and the second sleeve 41 may be closer to the top than the bottom of the first sleeve 40. Such an arrangement may provide additional space for the second sleeve 41 to bend downwards under gravity without contacting the first sleeve 40.

The first and second sleeves 40, 41, and although not illustrated optionally the intermediate sleeve 42, may comprise at least one rib 70 extending therearound. The at least one rib 70 may extend around the external surface 51 of the first, second and/or intermediate sleeves 40, 41, 42. Each of the first and second sleeves 40, 41 may comprise at least three ribs 70. The at least one rib 70 may be at least 1.5 times or at least twice the thickness of the surrounding area of the first, second and/or intermediate sleeves 40, 41, 42. In the present disclosure thickness refers to the thickness of the tubular walls of the sleeve arrangement 21 rather than the overall width of the sleeve arrangement 21.

The first, second and intermediate sleeves 40, 41, 42 may be formed and/or moulded integrally as illustrated such that, as best shown in FIG. 6, they may together form in the extended configuration a tube with a varying diameter along its length. The first, second and intermediate sleeves 40, 41, 42 may be formed integrally by moulding, preferably injection moulding, in the retracted configuration. Alternatively, they may be formed in the extended configuration by dip moulding. The moulding method may be, for example, compression moulding (such as silicon compression moulding), injection moulding (such as rubber injection moulding), dip moulding and/or transfer moulding. However, the first, second and/or intermediate sleeves 40, 41, 42 may alternatively be formed and/or moulded separately and subsequently connected together. For example, the first and second sleeves 40, 41 may be each be separately formed by welding a, for example polyvinyl chloride, sheet into the appropriate shape. They may then be connected to an annular disc, which may be rigid or flexible.

The barrier system 10 may comprise a sleeve holder 74 for selectively securing the glove arrangement 20, preferably the sleeve arrangement 21 thereof, to the barrier wall 15. The sleeve holder 74 may enable the sleeve glove end 44 of the sleeve arrangement 21 to be selectively mounted to the barrier wall 15 such that in the retracted configuration the second sleeve 41 is separated from the first sleeve 40. The sleeve holder 74 may comprise a strap 75 connected at or adjacent to the sleeve glove end 44, optionally to the cuff 23 and/or second sleeve 41. The sleeve holder 74 may comprise a strap mount 76 on the barrier wall 15. The operator may be able to selectively secure the strap 75 to the strap mount 76 in the retracted configuration. The sleeve holder 74 may alternatively comprise a hanger or support that holds the sleeve arrangement 21 otherwise such that the second sleeve 42 is held separately from the first sleeve 41. The sleeve holder 74 may therefore assist in maintaining the open cavity 48 between the first and second sleeves 40, 41 from the intermediate sleeve 42 to the sleeve glove end 44.

The sleeve arrangement 21 may be sufficiently flexible to enable the operator to orientate it between the retracted and extended configurations. The first sleeve 40 may be sufficiently flexible such that it can be turned inside out between the retracted and extended configurations. The first and second sleeves 40, 41 may be sufficiently flexible to enable the operator to manipulate them whilst performing work with the glove 22 in the work process area 12.

The sleeve arrangement 21 may also be sufficiently stiff, rigid or resilient to maintain its shape in the retracted configuration such that the first, second and intermediate internal surfaces 90, 91, 92 do not contact one another. The sleeve arrangement 21 may be resiliently biased to return to maintaining the, preferably entire, separation between the first, second and intermediate sleeves 40, 41, 42, optionally when supported by the sleeve holder 74. If the barrier system 10 comprises the sleeve holder 74, the sleeve arrangement 21 may only be sufficiently stiff to maintain its shape in the retracted configuration whilst the sleeve holder 74 secures the sleeve glove end 44 to the barrier wall 15. The first sleeve 40 may be sufficiently stiff such that it maintains its tubular shape in the retracted configuration. The second sleeve 41 may be sufficiently stiff to at least maintain its tubular shape and, if the barrier system 10 does not comprise the sleeve holder 74, maintain its separation from the first sleeve 40.

This balance between flexibility and stiffness may be achieved by appropriate selection of the materials and dimensions of the sleeve arrangement 21. In addition, the at least one rib 70 may be arranged to contribute towards the required stiffness.

In a particular example the barrier system 10 comprises a sleeve holder 74 and the first, second and intermediate sleeves 40, 41, 42 are moulded integrally as illustrated. The sleeve arrangement 21 is injection moulded in the retracted configuration shown in FIGS. 3 to 5 and has a circular cross-section. The first, second and intermediate sleeves 40, 41, 42 are formed from silicone having a hardness of 40 Shore A and are 1.5 mm thick. The first and second sleeves 40, 41 comprise five and four convex ribs 70 respectively, each rib having a thickness of 4 mm and a radius of curvature of 5 mm. The sleeve wall coupling 45 and sleeve glove coupling 46 each comprise an integral O-ring having diameters of 5 mm each. The sleeve wall end 43 and a sleeve glove end 44 have diameters of 265 mm and 106 mm respectively. The length of each of the first and second sleeves 40, 41 (i.e. the distance parallel to their centrelines) is 240 mm. The outer and inner perimeters 61, 62 are 228 mm and 156 mm respectively and the radius of curvature of the intermediate sleeve 42 varies from 9.5 mm at the outer perimeter 61 to 22 mm at the inner perimeter 62.

If the barrier system 10 does not comprise a sleeve holder 74 then the thickness of the first, second and intermediate sleeves 40, 41, 42 may be at least 4 mm [. Such thickness enables the sleeve arrangement 21 to maintain its shape in the retracted configuration without the sleeve holder 74. In addition, helical wire reinforcement or the like may be provided in the sleeve arrangement 21 for additional support.

In alternative suitable embodiments the first, second and/or intermediate sleeve 40, 41, 42 may have a thickness, other than at any ribs 70 if present, in the range of from approximately 0.2 mm to approximately 2 mm. The first, second and/or intermediate sleeve 40, 41, 42 may comprise polyurethane, silicone, natural rubber latex, neoprene, nitrile, polyurethane, polyvinyl chloride, ethylene propylene diene rubber, chlorosulfonated polyethylene and/or the like.

In accordance with the present disclosure, and as illustrated in FIGS. 2 and 3, the glove arrangement 20 may comprise an insert 80 mounted to the cuff 23 and/or sleeve arrangement 21 and at least partially extending into the glove 22 for supporting the glove 22 during decontamination. The insert 80 may support the glove 22, preferably the top of the glove 22 in use, such that it does not fold back upon and contact itself and/or does not contact the barrier wall 15 and/or glove arrangement 20. Occlusions on the underside of the glove 22 wrist and between the fingers may be avoided and occlusions between the glove 22 and other surfaces may be avoided, thereby improving the effectiveness of decontamination.

Figure 7:
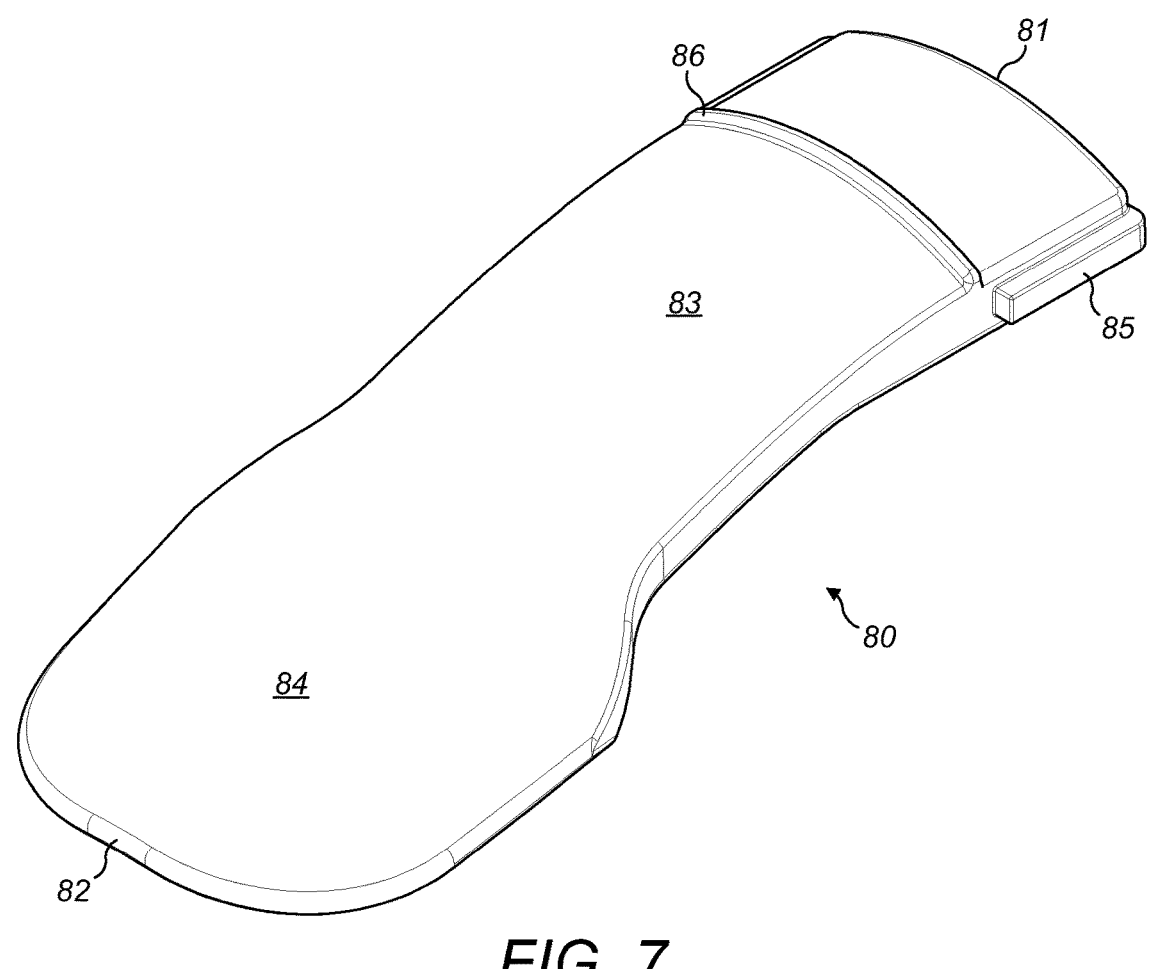
FIGS. 7, 8 and 9 are perspective, side and top plan views respectively of an insert of the barrier system of FIG. 1.
Figure 8:
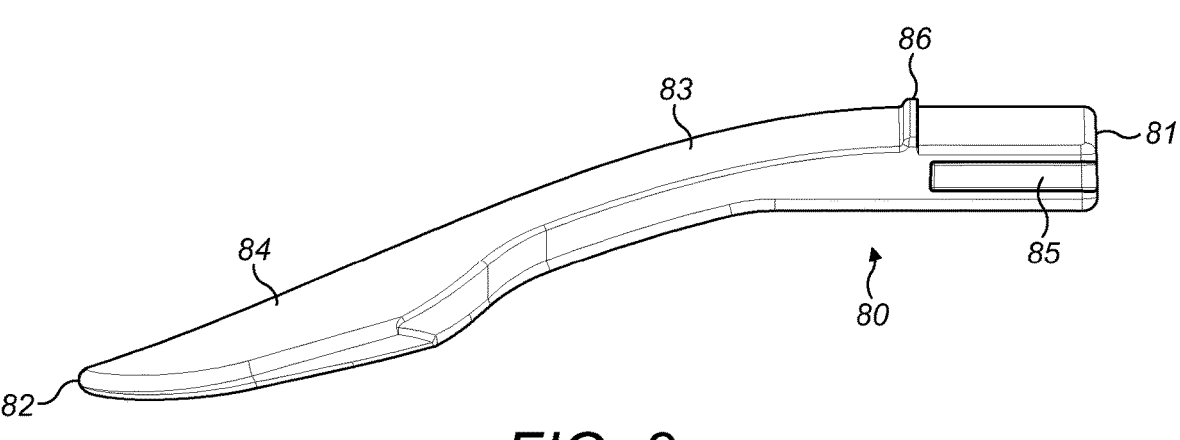
Figure 9:
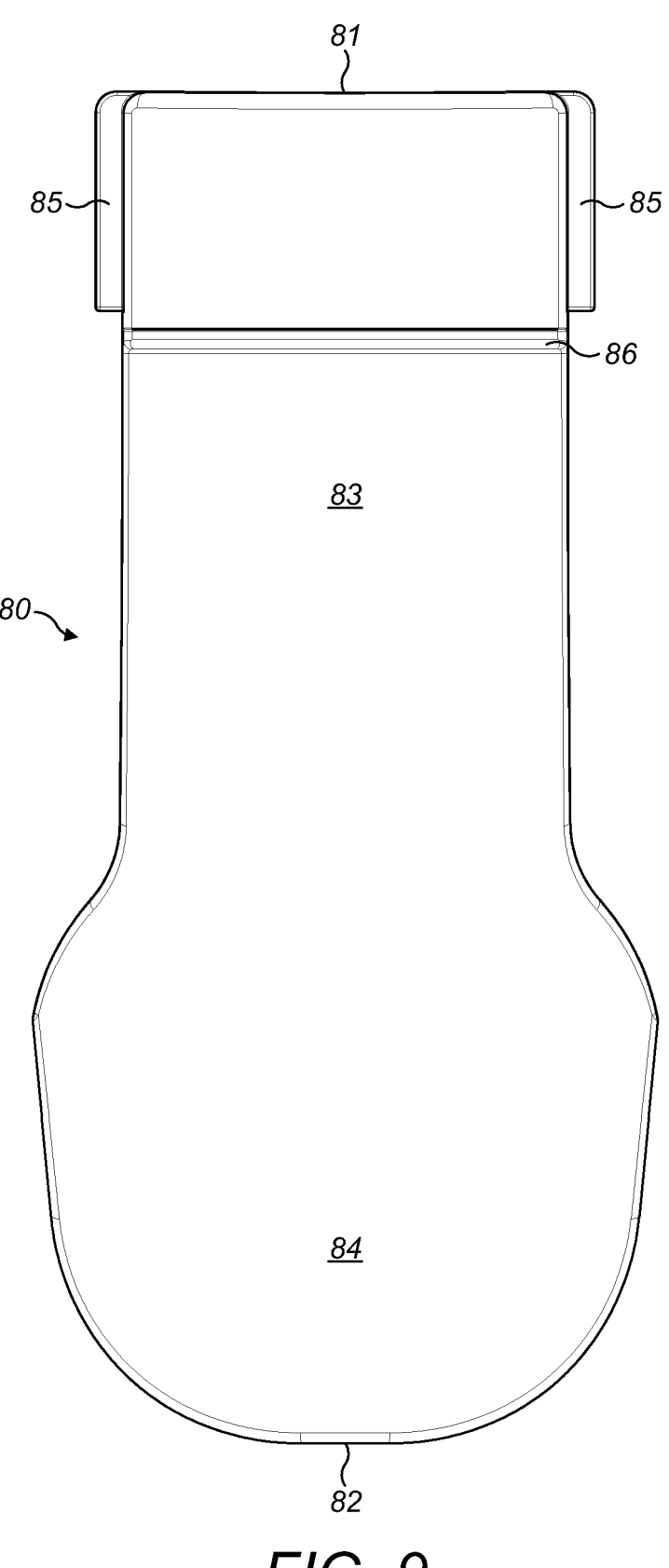

As illustrated in FIGS. 7 to 9, the insert 80 may extend between an insert inner end 81, which may be for mounting to the cuff 23 and/or sleeve arrangement 21, and an insert outer end 82, which may be for extending into the glove 22. The insert 80 may comprise an insert wrist portion 83, for contacting the wrist of the glove 22, extending from the insert inner end 81 and an insert hand portion 84, for contacting the upper hand of the glove, extending from the insert wrist portion 83 to the insert outer end 82. As best illustrated in FIG. 9, the insert hand portion 84 may be wider (i.e. wider along a horizontal plane) than the insert wrist portion 83.

As best illustrated in FIGS. 3 and 8, the insert 80 may curve downwardly from the insert inner end 81 to the insert outer end 82 and may curve downwardly from the cuff 23 and/or sleeve arrangement 21 in use. The thickness of the insert 80 may decrease from the insert inner end 81 to the insert outer end 82 of from the cuff 23 and/or sleeve arrangement 21.

The insert 80 may comprise an insert coupling 85 at the insert inner end 81 for selectively mounting to an insert mount 87 of the glove arrangement 20. The insert coupling 85 may comprise ridges along at least one side of the insert 80 as illustrated. The insert 80 may comprise an insert stop 86 for preventing the insert 80 from being pushed into the insert inner end 81 beyond a predetermined distance.

The insert mount 87 may be formed on the cuff 23 as illustrated and/or on the sleeve arrangement 21. The insert mount 87 may comprise at least one flange having a slot or the like. The insert mount 87 may be mounted in the upper half and/or at the top of the cuff 23 and/or sleeve arrangement 21. Alternatively, the insert mount 87 may comprise a ring or the like extending around the inside or outside of the cuff 23 and/or sleeve arrangement 21 for the insert 80 to couple to.

In use the insert 80 may be mounted to the insert mount 87 when the glove arrangement 20 is in the retracted configuration, as in FIG. 3. Thus, during decontamination, the insert 80 may prevent occlusions from forming around the glove 22. The insert 80 may be removed for moving the glove arrangement 20 into the extended configuration, as in FIG. 6. However, the insert 80 may also be maintained in the insert mount 87 when the glove arrangement 20 is in the extended configuration, particularly if it is sufficiently flexible to not interfere with the operator's manipulation of the glove 22.

The insert 80 may be formed integrally with the cuff 23 and/or sleeve arrangement 21, rather than being coupled by an insert mount 87, such that it cannot be removed during use.

If the glove arrangement 20 comprises a gauntlet, the insert mount 87 may be formed on the glove 22, cuff 23 and/or sleeve arrangement 21. The insert 80 may instead be formed integrally with the glove 22, cuff 23 and/or sleeve arrangement 21. In a gauntlet the cuff 23 and sleeve arrangement 21 may be considered the cuff and sleeve areas of the gauntlet.

In use the operator may insert their arms and hands into the glove arrangement 20 and adjust the sleeve arrangement 21 into the extended configuration. The operator may then use the gloves 22 to perform work in the work process area 12. The operator may then retract the sleeve arrangement 21 into the retracted configuration for storage and/or decontamination. The operator may connect the insert 80 to support the glove 22 and/or may attach the sleeve holder 74 to assist in maintaining the sleeve arrangement 21 in the retracted configuration. Subsequently a decontaminant, such as from the decontamination system 18, may be directed into the work process area 12 and onto the barrier wall 15 and internal surface 50. As the first, second and intermediate internal surfaces 90, 91, 92 are entirely separated from each other no occlusions are formed to block decontaminant from reaching them. In addition, the insert 80 may support the glove 22 such that it has no occlusions. As a result, effective and complete decontamination of the glove arrangement 20 may be achieved.

The invention claimed is:

1. A glove arrangement for mounting to a barrier wall of a barrier system defining a work process area, said glove arrangement comprising a sleeve arrangement, the sleeve arrangement comprising:

a first sleeve for mounting around an aperture through the barrier wall and comprising a first internal surface;

a second sleeve for mounting a glove thereto and comprising a second internal surface; and an intermediate sleeve comprising an intermediate internal surface, an outer perimeter attached to the first sleeve and an inner perimeter attached to the second sleeve, the outer perimeter having a greater diameter than the inner perimeter, wherein the sleeve arrangement is configured to be movable between:

an extended configuration in which the second sleeve extends from the first and intermediate sleeves for use during manipulation of the glove by an operator and the first, second and intermediate internal surfaces are exposed to the environment in the work process area; and a retracted configuration in which:

the second sleeve is positioned at least partially inside the first sleeve about the intermediate sleeve such that the first and second internal surfaces at least partially face each other; and the intermediate sleeve separates the intermediate internal surface from itself and from the first and second internal surfaces to form a cavity between the first, second and intermediate internal surfaces with the intermediate internal surface facing the cavity; and wherein the intermediate sleeve is resiliently biased, or is rigid, to maintain the separation of the intermediate internal surface from itself and from the first and second internal surfaces when the sleeve arrangement is in the retracted configuration without an external support contacting the surface of the intermediate sleeve.

2. A glove arrangement as claimed in claim 1 wherein a rate of reduction of diameter along the length of the sleeve arrangement is greater along the intermediate sleeve than along the first and/or second sleeve.

3. A glove arrangement as claimed in claim 1 wherein the first and second sleeves are sufficiently flexible for manipulation by the operator and sufficiently stiff to separate the first and second internal surfaces from one another.

4. A glove arrangement as claimed in claim 1 wherein the minimum separation distance between the first and second internal surfaces in the retracted configuration is at least 3 mm.

5. A glove arrangement as claimed in claim 1 wherein the first sleeve tapers towards the intermediate sleeve and/or the second sleeve tapers from the intermediate sleeve.

6. A glove arrangement as claimed in claim 1 wherein a length of the first and/or second sleeve is at least twice a length of the intermediate sleeve.

7. A glove arrangement as claimed in claim 1 wherein the intermediate sleeve forms a tapered tubular body in the extended configuration and forms a curved annular body in the retracted configuration or wherein the intermediate sleeve comprises a rigid ring.

8. A glove arrangement as claimed in claim 1 wherein the first, second and intermediate internal surfaces face outwardly away from themselves in the extended configuration.

9. A glove arrangement as claimed in claim 1 wherein in the retracted configuration at least 50% of the second sleeve is located within the first sleeve, and wherein in the extended configuration at least 50% of the second sleeve is outside of the first sleeve.

10. A glove arrangement as claimed in claim 1 wherein the centre of the inner perimeter is vertically offset from the centre of the outer perimeter.

11. A glove arrangement as claimed in claim 1 wherein the first and/or second sleeves comprises at least one rib.

12. A glove arrangement as claimed in claim 1 wherein the first, second and intermediate sleeves are formed integrally and/or moulded together.

13. A glove arrangement as claimed in in claim 1 and a glove mounted to the second sleeve.

14. A glove arrangement as claimed in claim 13 wherein the glove is integrally formed with the sleeve arrangement or the glove is mounted to the second sleeve via a cuff.

15. A glove arrangement as claimed in claim 13 further comprising an insert mounted to the sleeve arrangement and at least partially extending into the glove for supporting the glove in the retracted configuration.

16. A method of manufacturing the glove arrangement of claim 1 wherein the method comprises moulding the sleeve arrangement in the retracted configuration.

17. A barrier system comprising:

a barrier wall at least partially separating an operator area from a work process area and comprising at least one aperture therethrough; and at least one glove arrangement according to claim 1, the first sleeve being mounted to the barrier wall around the at least one aperture, wherein in the extended configuration the second sleeve, intermediate sleeve and at least part of the first sleeve are located in the work process area and in the retracted configuration the intermediate sleeve and at least part of the first and second sleeves are located in the operator area.

18. A barrier system as claimed in claim 17 further comprising a sleeve holder for selectively securing the glove arrangement to the barrier wall in the retracted configuration.

19. A method of operating the barrier system of claim 17 comprising:

configuring the sleeve arrangement in the extended configuration and manipulating the glove arrangement to perform work in the work process area; and configuring the sleeve arrangement in the retracted configuration and directing a decontaminant into the work process area to decontaminate the first, second and intermediate internal surfaces.

* * * * *